(12) United States Patent
Yang et al.

(10) Patent No.: US 10,542,890 B2
(45) Date of Patent: Jan. 28, 2020

(54) MAGNETIC RESONANCE IMAGE (MRI) COIL APPARATUS

(71) Applicant: Quality Electrodynamics, LLC, Mayfield Village, OH (US)

(72) Inventors: Xiaoyu Yang, Indiana, PA (US); Tsinghua Zheng, Aurora, OH (US)

(73) Assignee: Quality Electrodynamics, LLC, Mayfield Village, OH (US)

( * ) Notice: Subject to any disclaimer, the term of this patent is extended or adjusted under 35 U.S.C. 154(b) by 1080 days.

(21) Appl. No.: 14/945,462

(22) Filed: Nov. 19, 2015

(65) Prior Publication Data
US 2017/0143203 A1    May 25, 2017

(51) Int. Cl.
*A61B 5/00*    (2006.01)
*G01R 33/34*    (2006.01)
*A61B 5/055*    (2006.01)

(52) U.S. Cl.
CPC .............. *A61B 5/004* (2013.01); *A61B 5/055* (2013.01); *G01R 33/34* (2013.01)

(58) Field of Classification Search
None
See application file for complete search history.

(56) References Cited

U.S. PATENT DOCUMENTS

| | | | | |
|---|---|---|---|---|
| 5,594,339 | A * | 1/1997 | Henderson | G01R 33/34084 324/318 |
| 6,591,128 | B1 * | 7/2003 | Wu | G01R 33/34084 324/318 |
| 2005/0107686 | A1 * | 5/2005 | Chan | G01R 33/3415 600/422 |
| 2005/0187459 | A1 * | 8/2005 | Trequattrini | G01R 33/3806 600/415 |
| 2007/0039101 | A1 * | 2/2007 | Luginbuhl | A61B 5/0555 5/600 |
| 2011/0006771 | A1 * | 1/2011 | Randell | G01R 33/3403 324/318 |
| 2011/0241683 | A1 * | 10/2011 | Nnewihe | G01R 33/3415 324/318 |

* cited by examiner

*Primary Examiner* — Jason T Yen
(74) *Attorney, Agent, or Firm* — Eschweiler & Potashnik, LLC

(57) ABSTRACT

An example magnetic resonance imaging (MRI) coil base apparatus for use with interchangeable attachable and detachable coil attachments is described. The coil base apparatus electrically and mechanically couples to different MRI coil attachments designed for imaging different body parts (e.g., ankles, knees, wrists, elbows, shoulders). The MRI coil base apparatus includes elements (e.g., channel, pre-amplifier, mixer, feed circuit, decoupling circuit) for controlling the coil attachment to transmit radio frequency (RF) energy that produces nuclear magnetic resonance (NMR) in an object exposed to the RF energy. The coil attachment includes elements that transmit the RF energy and a copper trace that receives resulting NMR signals. The coil base apparatus may include a slide apparatus for repositioning the coil attachment in one axis when the coil attachment is coupled to the coil base apparatus or a pivot apparatus for rotating the coil attachment when it is coupled to the coil base apparatus.

32 Claims, 14 Drawing Sheets

MAGNETIC RESONANCE IMAGE (MRI) COIL APPARATUS

BACKGROUND

Magnetic resonance imaging (MRI) involves the transmission and receipt of radio frequency (RF) energy. RF energy may be transmitted by a coil. Resulting magnetic resonance (MR) signals may also be received by a coil. Conventionally, MR coils have had a set of elements that included a copper trace arranged in a loop in which an electric current could be induced by nuclear magnetic resonance (NMR) signals produced by an object near the loop. The set of elements also included other items including capacitors, resistors, pre-amplifiers, a PIN diode, or additional signal processing elements. Conventionally, each coil had all of the elements.

Different MRI procedures may employ different coils. In conventional MRI practice, different coils may be used to image the foot, the ankle, the knee, the hip, the hand, the wrist, the elbow, the shoulder, the neck, the chest, the abdomen, the upper leg, the lower leg, the upper arm, the lower arm, fingers, toes, or other body parts. Conventionally, storing this large collection of coils takes up valuable space in a health care imaging center. Conventionally, selecting and arranging the appropriate coil for a procedure takes time, expertise, and some strength, especially for heavier coils.

BRIEF DESCRIPTION OF THE DRAWINGS

The accompanying drawings, which are incorporated in and constitute a part of the specification, illustrate various example systems, methods, and other embodiments of various aspects of the invention. It will be appreciated that the illustrated element boundaries (e.g., boxes, groups of boxes, or other shapes) in the figures represent one example of the boundaries. One of ordinary skill in the art will appreciate that in some embodiments one element may be designed as multiple elements, multiple elements may be designed as one element, an element shown as an internal component of another element may be implemented as an external component and vice versa, and so on. Furthermore, elements may not be drawn to scale.

DETAILED DESCRIPTION

Example apparatus provide an MRI coil base apparatus that is configured for use with interchangeable coils that are attachable and detachable to and from the MRI coil base apparatus. An interchangeable coil may be attached to the base for an MRI procedure and then may be removed and replaced by a different interchangeable coil for a subsequent MRI procedure. A conventional radiology department may have a set of MRI coils. Example apparatus facilitate the radiology department having a smaller, less expensive suite of MRI coils that improve operator workflow.

Figure 1:
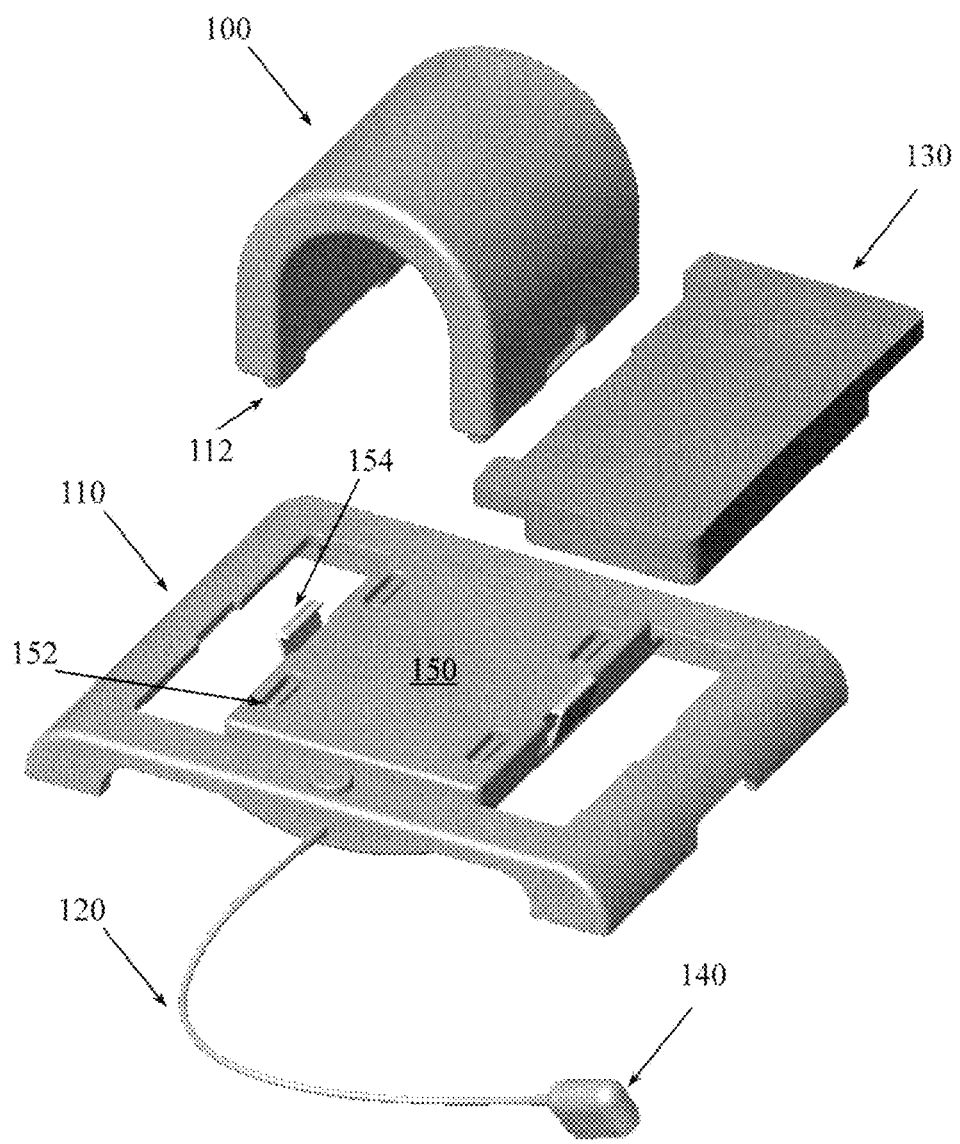
FIG. 1 illustrates an example coil that may be used with an example base configured for use with interchangeable attachable and detachable coils.

FIG. 1 illustrates an example coil 100 that may be used with an example base 110 that is configured for use with interchangeable attachable and detachable coils. Coil 100 may be used to image a knee. Coil 100 includes a connector 112 that provides electrical or mechanical connections to the MRI coil base apparatus 110 at, for example, connector 152. While a single connector 112 is illustrated, a greater number of connectors may be employed.

Connector 112 may mechanically or electrically connect coil 108 to the MRI coil base apparatus 110. Connector 112 and connector 152 may provide an electrical connection. The electrical connection may be, for example, a direct current (DC) connection. The electrical connection may also be, for example, a conductive connection, a capacitive coupling connection, or an inductive coupling connection. The electrical connection may pass a radio frequency (RF) signal between coil 100 and base 110. The RF signal may be unamplified.

Base 110 may also include a latch 154 or other mechanical attachment mechanism that allows coil 100 to be attached and detached from base 110. Base 110 may include a portion 150 that is configured to slide to the right or left to allow a right knee or a left knee to be imaged using coil 100. More generally, portion 150 may slide or otherwise move to allow an attached coil to be repositioned in base 110. Spacer 130 may be placed into base 110 to help hold coil 100 in either the right side or left side configuration.

Base 118 has a cable 120 that connects to connector 140. Connector 140 may in turn connect the base 110 to an MRI apparatus (e.g., apparatus 1200, FIG. 12).

In a conventional system that does not have a base 110, all of the circuits, electronics, or other elements for the coil 100 would be located in coil 100. However, some circuits, electronics, or other elements may be common to different coils that are available for different MRI procedures. Therefore, some circuits, electronics, or other elements that are common to the different coils may be located in base 110, base 150, cable 120, or connector 140. This may facilitate reducing the overall cost of a set of coils by eliminating duplicate circuits, electronics, or other elements.

Figure 2:
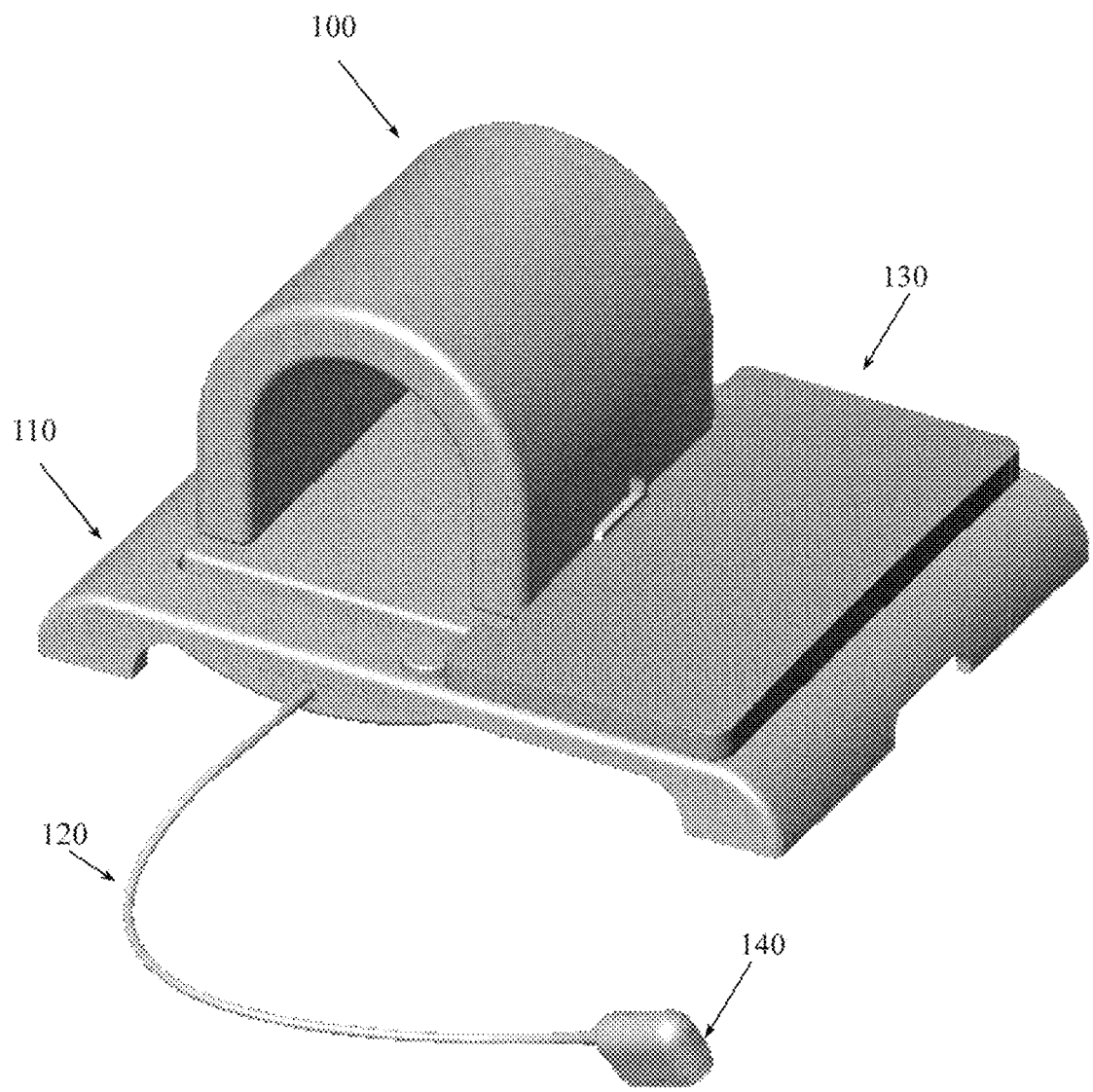
FIG. 2 illustrates an example coil attached to an example base configured for use with interchangeable attachable and detachable coils.

FIG. 2 illustrates coil 100 attached to base 110 with spacer 130 in place. Circuits, electronics, or other elements in coil 100 may be in electrical or data communication with base 110 through connectors 112 and 152. The assembly of coil 100 and base 110 may in turn be in electrical or data communication with an MRI apparatus (e.g., apparatus 1200, FIG. 12) through cable 120 and connector 140. Coil 100 is illustrated on the left side of base 110 with spacer 130 on the right side. Coil 100 may also be positioned on the right side of base 110 with space 130 on the left side. This facilitates using a single coil for either the left knee or the right knee.

Figure 3:
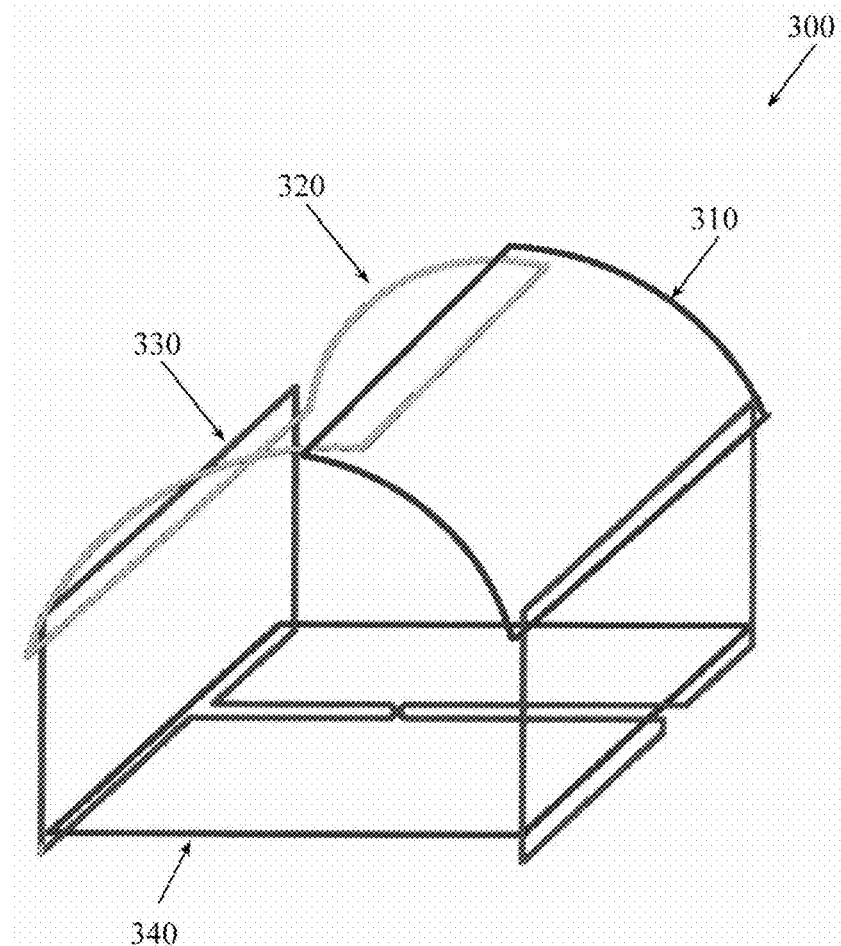
FIG. 3 illustrates a schematic of a portion of an example coil that may be used with an example base configured for use with interchangeable attachable and detachable coils.

FIG. 3 illustrates elements of an example coil 300 that may be used with an example base. Coil 300 may be used to image a knee. Coil 300 illustrates one example of traces, channels, and elements for coil 100 (FIG. 1). Coil 300 has 8 channels and includes two rows in the superior direction and in the inferior direction. The rows have the electrical layouts indicated by elements 310, 320, 330, and 340. Two channels may be provided by element 340, which may be part of the base (e.g., base 110, FIG. 1). Six channels may be provided by elements 310, 320, and 330, which are part of a coil attachment (e.g., coil 100) that may be mechanically and electrically coupled to the base (e.g., base 110). While four elements and eight channels are illustrated, and while certain layouts are illustrated, one skilled in the art will appreciate that other layouts may be employed.

Different coils may have different configurations. Different coils may connect to the same MRI coil base apparatus at different times. In one example, coils like coil 300 may share a channel(s) with the MRI coil base apparatus. When a suite of detachable and attachable coils all share the same channel or channels, this may reduce the total cost of coil ownership by, for example, reducing the cost of individual coils and producing a simpler work flow for operators tasked with using the members of the suite. This may also reduce the weight of the individual coils making the job easier for the operator. Once the base is attached to the MRI apparatus, lighter detachable/attachable coils can be attached to the base. The coils are lighter because some of the circuits, traces, electronics, or other elements are located in the base.

Figure 4:
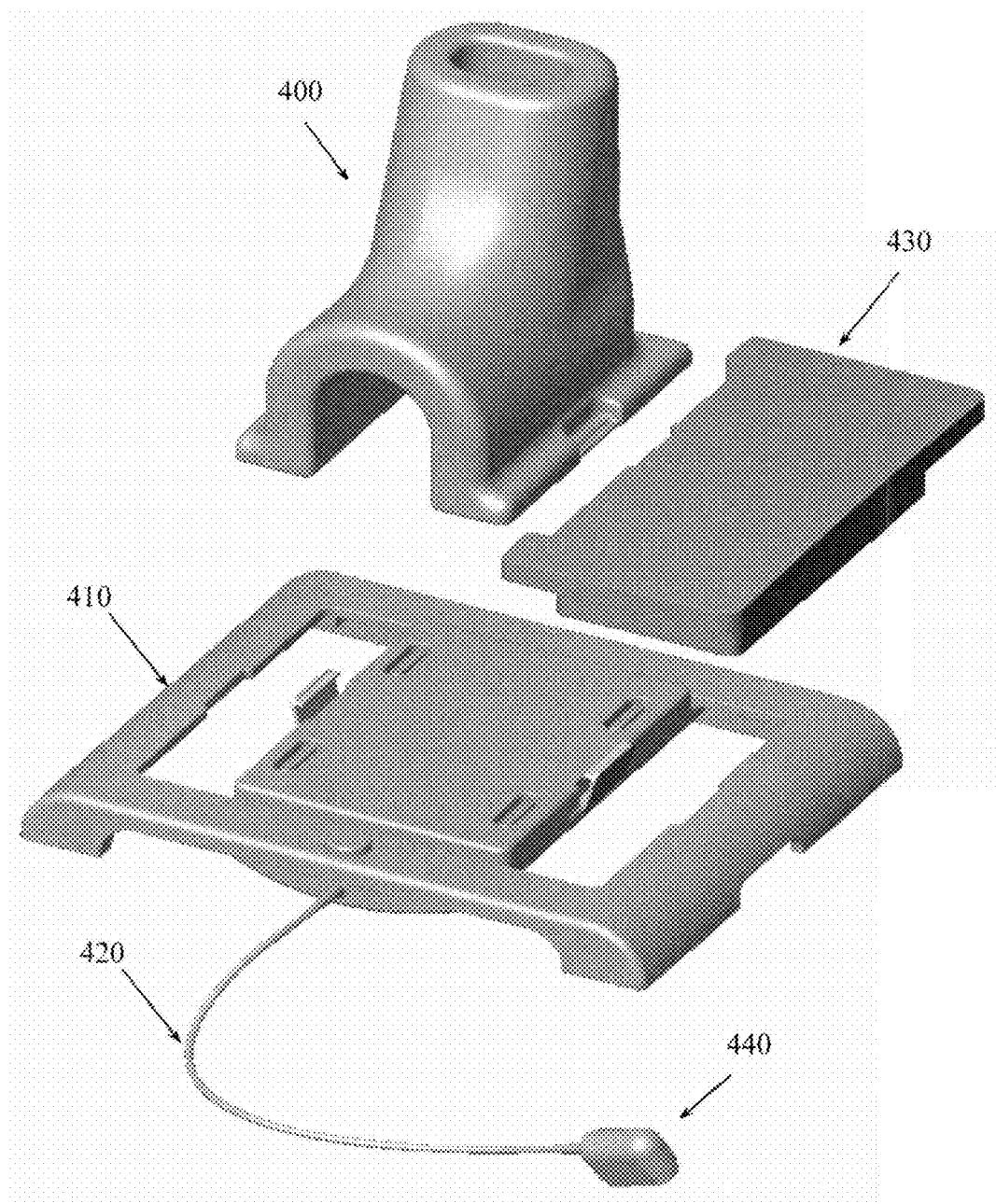
FIG. 4 illustrates an example coil that may be used with an example base configured for use with interchangeable attachable and detachable coils.

FIG. 4 illustrates an example coil 400 that may be used with an example base 410 configured for use with interchangeable attachable and detachable coils. Coil 400 may be used to image a foot. Base 410 may include a cable 420 and connector 440 for connecting to an MRI apparatus (e.g., apparatus 1200, FIG. 12). Base 410 may be base 110 (FIG. 1). Coil 400 may be positioned on the left or right of base 410 and then spacer 430 may be positioned to hold coil 400 in the desired position. Allowing base 410 to receive the coil 400 in either the left side or the right side facilitates using a single coil for imaging either the left foot or the right foot.

Figure 5:
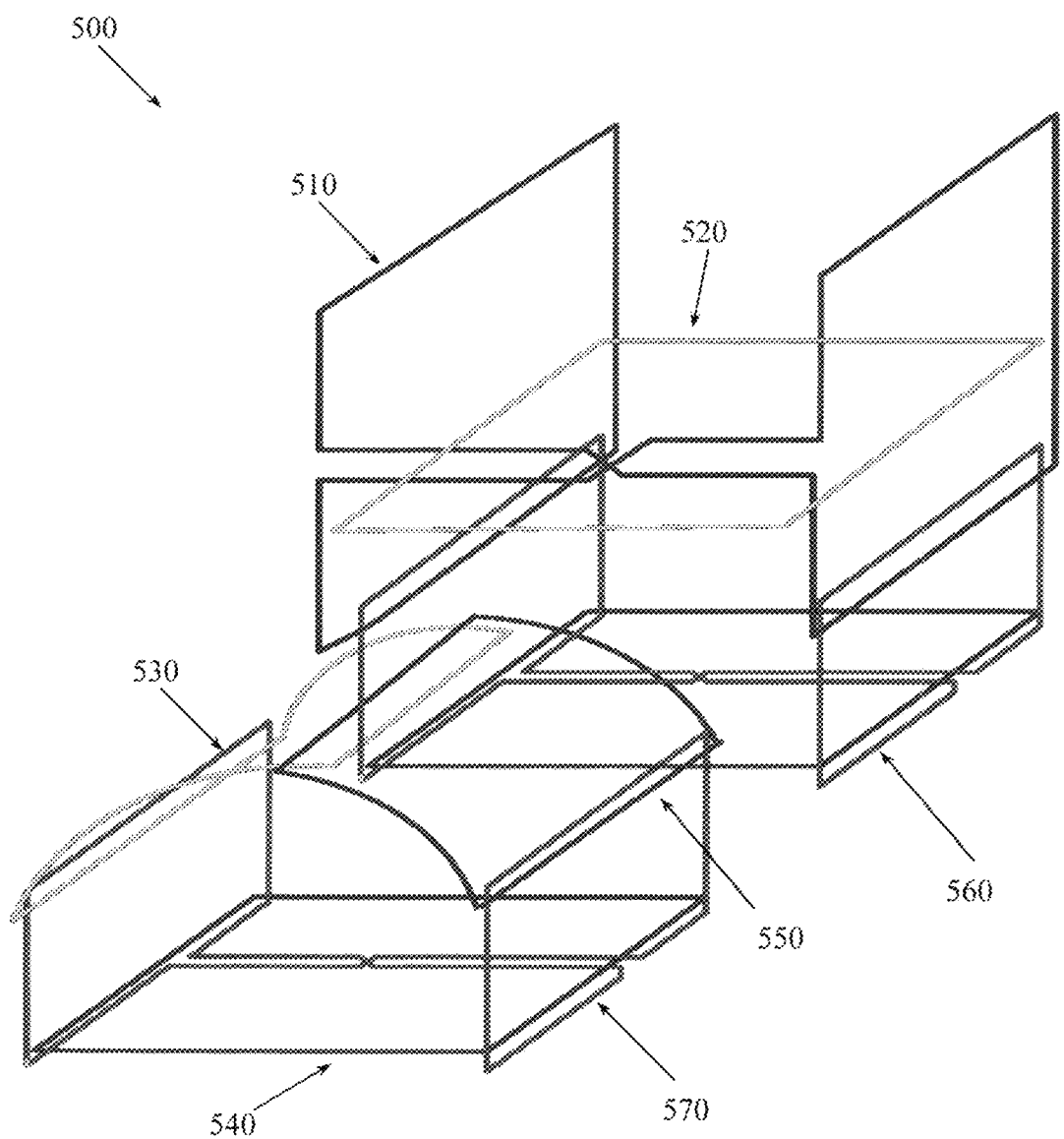
FIG. 5 illustrates a schematic of a portion of an example coil that may be used with an example base configured for use with interchangeable attachable and detachable coils.

FIG. 5 illustrates elements of an example coil 500 that may be used with an example base (e.g., base 410 FIG. 4, base 110 FIG. 1). Coil 500 may be used to image a foot. Coil 500 has 8 channels and includes two rows in the superior direction and in the inferior direction. The rows have the electrical layouts indicated by elements 510, 520, 530, and 540. Two channels may be provided by element 540 which may be part of the base (e.g., base 410 FIG. 4, base 110 FIG. 1). Six channels may be provided by elements 510, 520, and 530, which are part of a coil attachment (e.g., coil 400, FIG. 4) that may be mechanically and electrically coupled to the base (e.g., base 410 FIG. 4, base 110 FIG. 1). There may be overlaps between rows. The elements in FIG. 5 are shown in non-overlap mode for ease of presentation. While four elements and eight channels are illustrated, and while certain layouts are illustrated, one skilled in the art will appreciate that other layouts may be employed.

Figure 6:
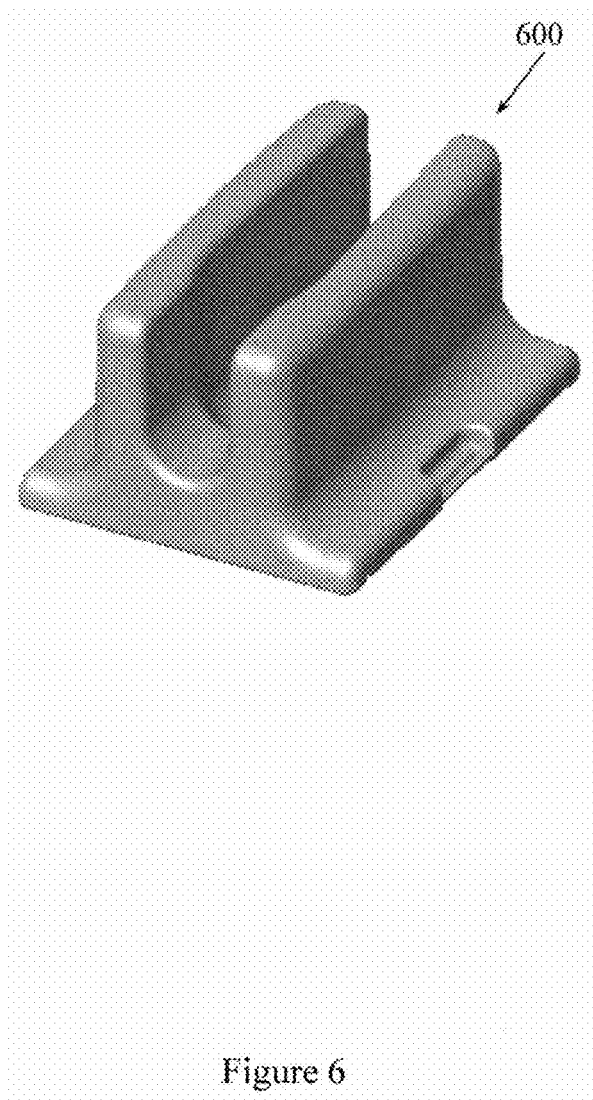
FIG. 6 illustrates an example coil that may be used with an example base configured for use with interchangeable attachable and detachable coils.

FIG. 6 illustrates an example coil 600 that may be used with an example base (e.g., base 410 FIG. 4, base 110 FIG. 1) configured for use with interchangeable attachable and detachable coils. Coil 600 may be used to image a wrist. Coil 600 may be used to image either a right wrist or a left wrist.

Figure 7:
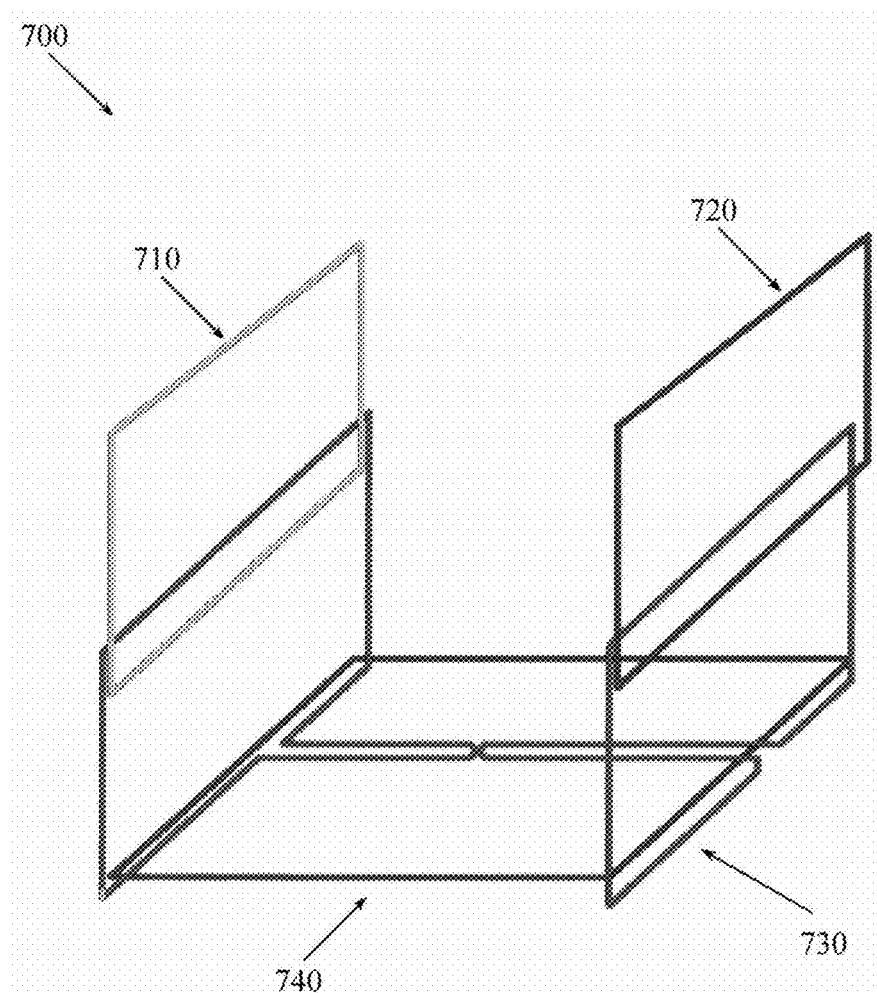
FIG. 7 illustrates a schematic of a portion of an example coil that may be used with an example base configured for use with interchangeable attachable and detachable coils.

FIG. 7 illustrates elements of an example coil 700 that may be used with an example base. Coil 700 may be used to image a wrist. Coil 700 has 8 channels and includes two rows in the superior direction and in the inferior direction. The rows have the electrical layouts indicated by elements 710, 720, 730, and 740. Two channels may be provided by element 740 which may be part of the base. Six channels may be provided by elements 710, 720, and 730, which are part of a coil attachment that may be mechanically and electrically coupled to the base. There may be overlaps between rows. The elements in FIG. 7 are shown in non-overlap mode for ease of presentation. While four elements and eight channels are illustrated, and while certain layouts are illustrated, one skilled in the art will appreciate that other layouts may be employed.

Figure 8:
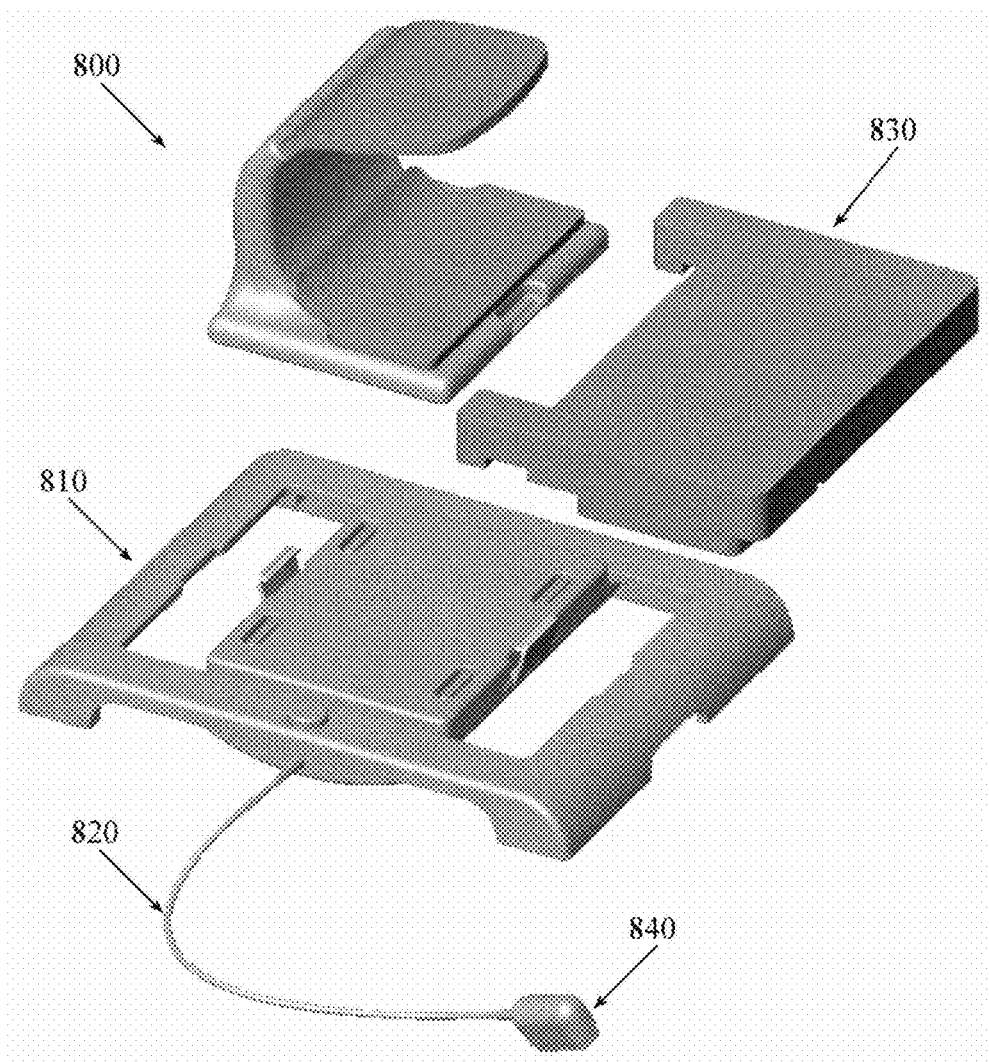
FIG. 8 illustrates an example coil that may be used with an example base configured for use with interchangeable attachable and detachable coils.

FIG. 8 illustrates an example coil 800 that may be used with an example base 810 configured for use with interchangeable attachable and detachable coils. Coil 800 may be used to image a shoulder. Base 810 may be connected to an MRI apparatus (e.g., 1200, FIG. 12) through cable 820 and connector 840. Conventionally, each coil may have had its own cable and connector. However, this may have increased the complexity and expense of owning multiple coils. Coil 800 and other coils described herein, do not have cables like cable 820 or connectors like connector 840. Instead, coil 800 and other coils described herein electrically and mechanically attach to a base (e.g., base 810) and then connect to the MRI apparatus through base 810, cable 820, and connector 840.

Figure 9:
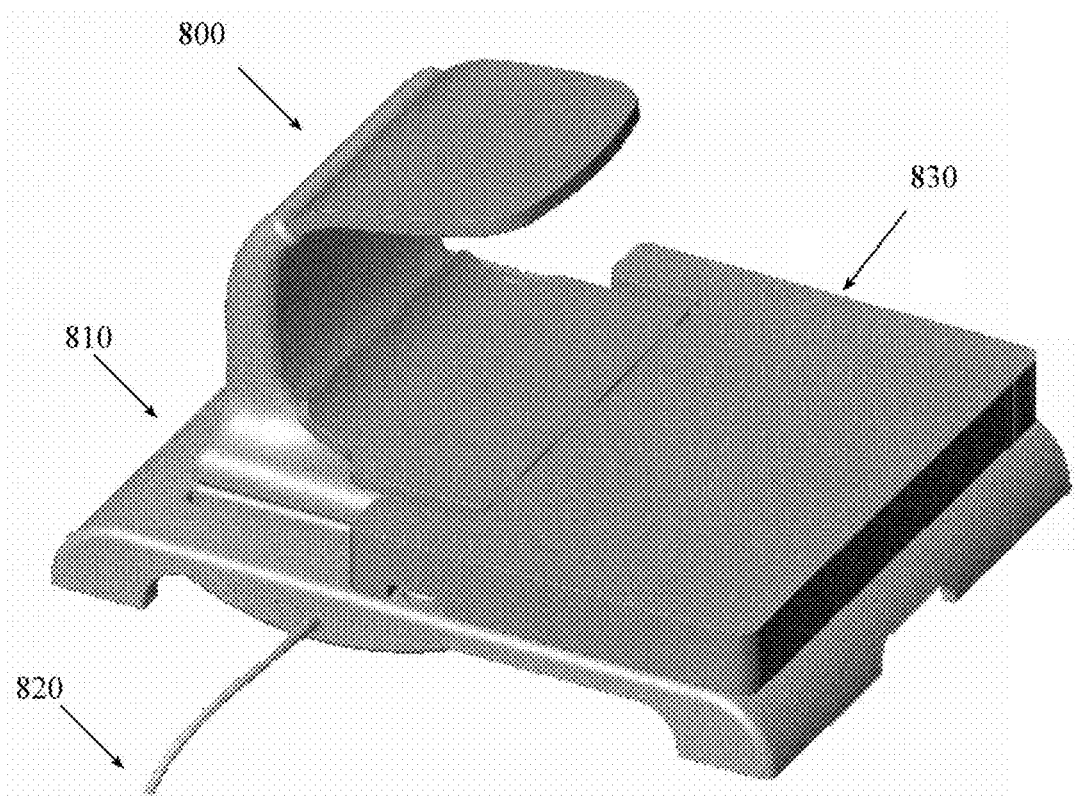
FIG. 9 illustrates an example coil attached to an example base configured for use with interchangeable attachable and detachable coils.
Figure 10:
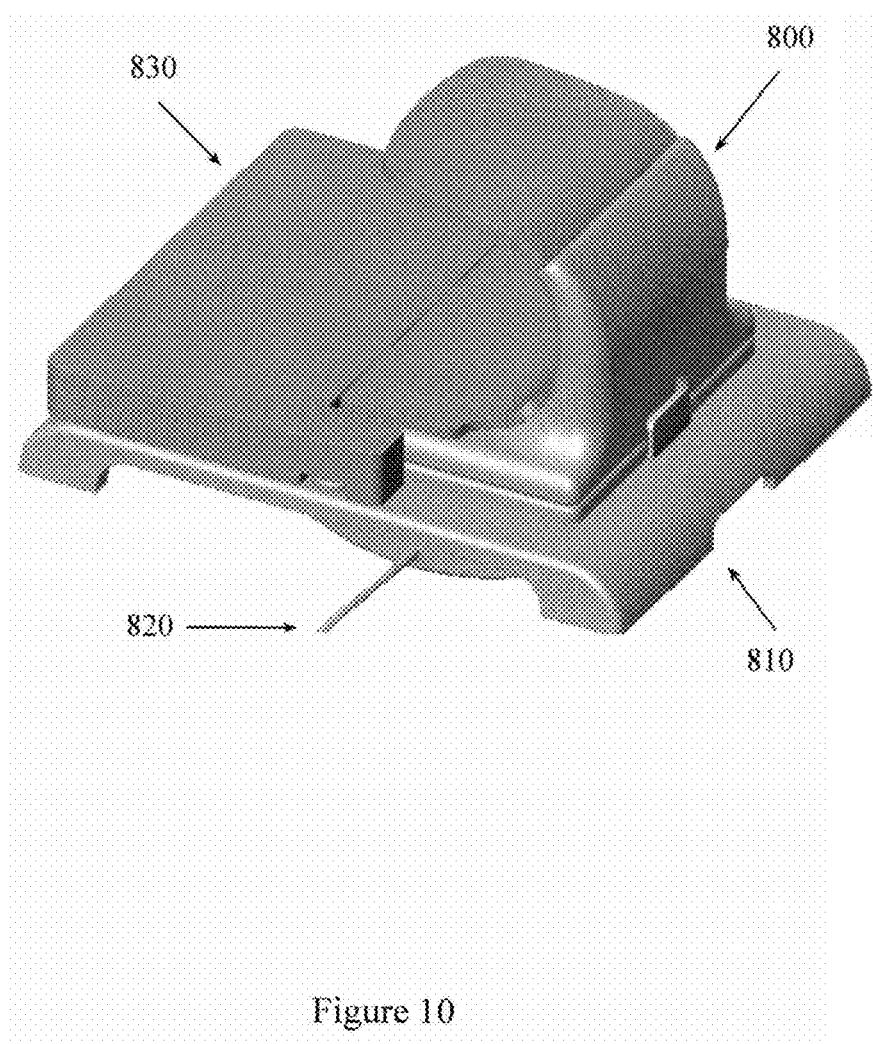
FIG. 10 illustrates an example coil attached to an example base configured for use with interchangeable attachable and detachable coils.

Coil 800 may be positioned to the left or right side of base 810. Spacer 830 may be positioned to hold coil 800 in either configuration. FIG. 9 illustrates coil 800 positioned on the left side of base 810 with spacer 830 on the right side of base 810. FIG. 10 illustrates coil 800 positioned on the right side of base 810 with spacer 830 on the left side of base 810. This demonstrates how a single shoulder coil may be used to image either the left shoulder or the right shoulder, which facilitates reducing the total number of coils needed to have a complete set, which in turn reduces acquisition cost, storage cost, and operator cost.

Figure 11:
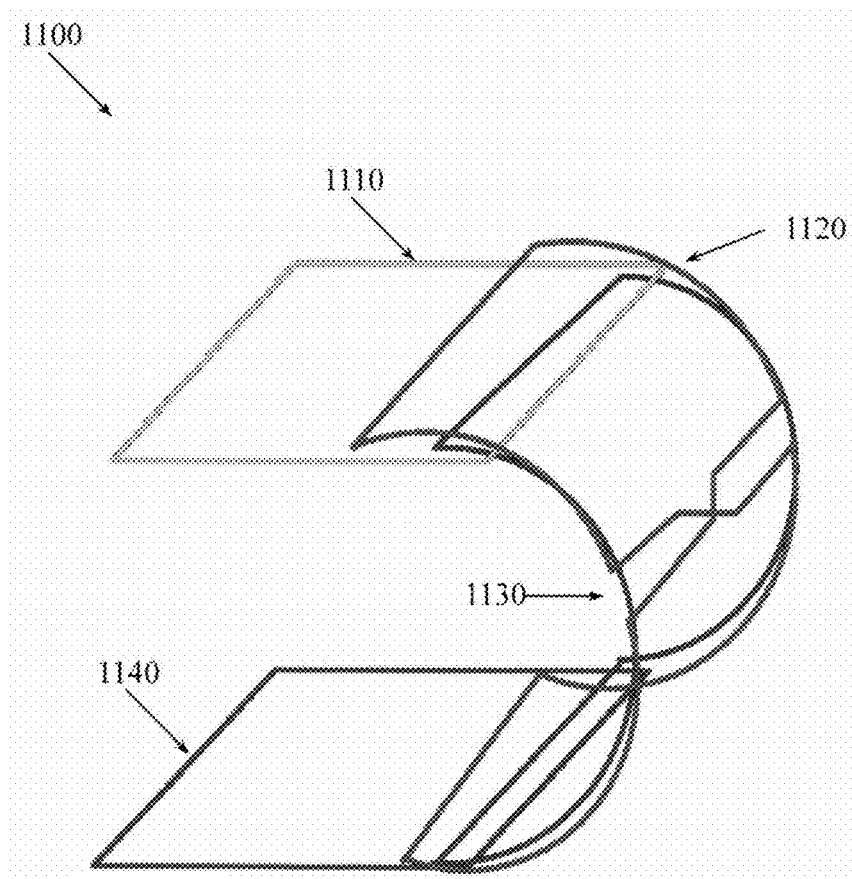
FIG. 11 illustrates a schematic of a portion of an example coil that may be used with an example base configured for use with interchangeable attachable and detachable coils.

FIG. 11 illustrates elements of an example coil 1100 that may be used with an example base (e.g., base 800, FIG. 8). Coil 1100 may be used to image a shoulder. Coil 1100 has 8 channels and includes two rows in the superior direction and in the inferior direction. The rows have the electrical layouts indicated by elements 1110, 1120, 1130, and 1140. Two channels may be provided by element 1140 which may be part of the base. Six channels may be provided by elements 1110, 1120, and 1130, which are part of a coil attachment that may be mechanically and electrically coupled to the base. There may be overlaps between rows. The elements in FIG. 11 are shown in non-overlap mode for ease of presentation. While four elements and eight channels are illustrated, and while certain layouts are illustrated, one skilled in the art will appreciate that other layouts may be employed.

Figure 12:
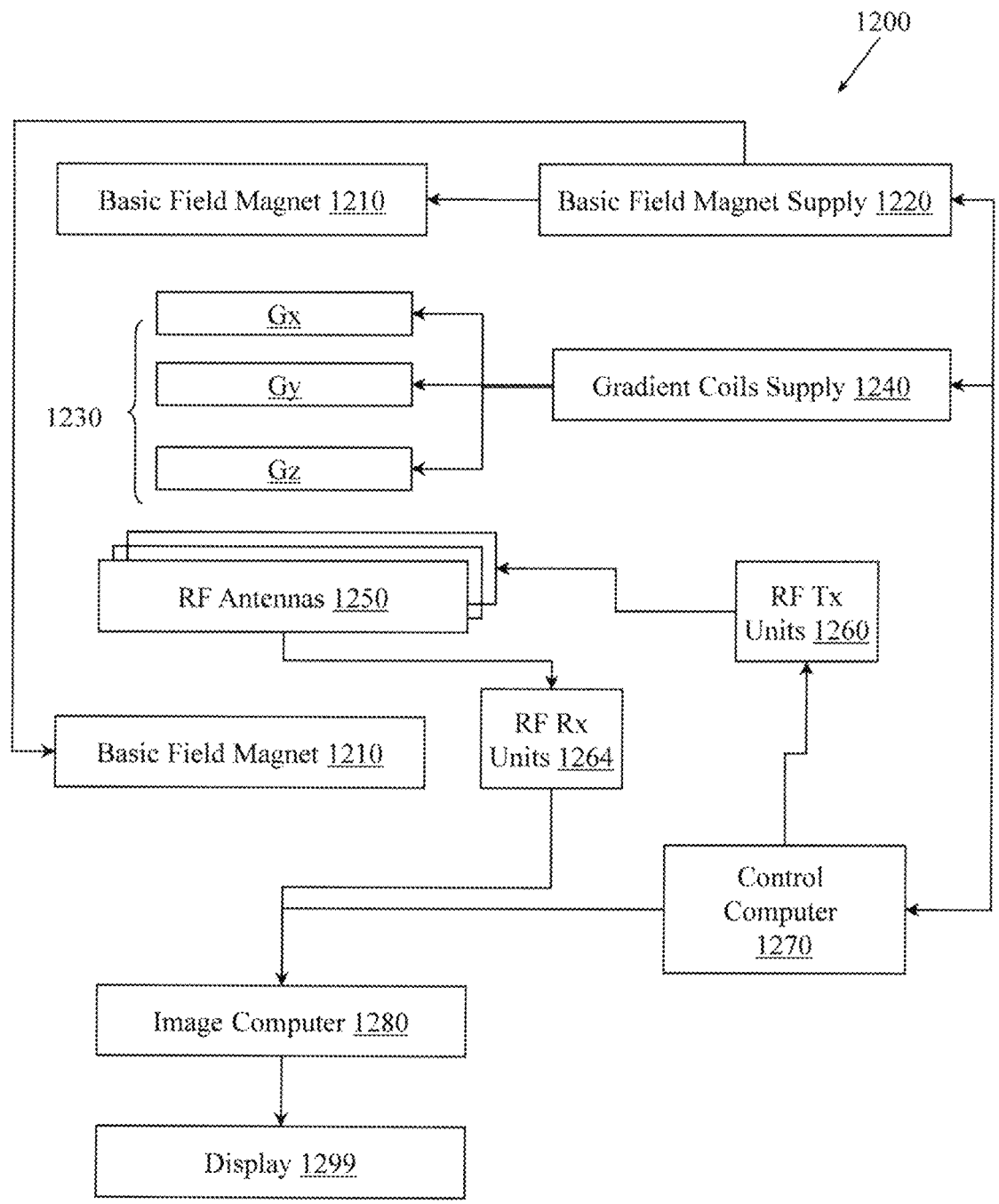
FIG. 12 illustrates an MRI apparatus configured to be coupled to an example base that is coupled to an example interchangeable coil.

FIG. 12 illustrates an example MRI apparatus 1200 to which an example MRI coil base apparatus (e.g., base 1300, FIG. 13) may be coupled. The apparatus 1200 includes a basic field magnet(s) 1210 and a basic field magnet supply 1220. Ideally, the basic field magnets 1210 would produce a uniform B0 field. However, in practice, the B0 field may not be uniform, and may vary over an object being imaged by the MRI apparatus 1200. MRI apparatus 1200 may include gradient coils 1230 configured to emit gradient magnetic fields like $G_S$, $G_P$ and $G_R$. The gradient coils 1230 may be controlled, at least in part, by a gradient coils supply 1240. In some examples, the timing, strength, and orientation of the gradient magnetic fields may be controlled and thus selectively adapted during an MRI procedure.

MRI apparatus 1200 may include a set of RF antennas 1250 that are configured to generate RF pulses and to receive resulting magnetic resonance signals from an object to which the RF pulses are directed. Members of the RF antennas 1250 may be located in an example base (e.g., base 1310 base 1350, FIG. 13) and in example coils (e.g., coil 100 FIG. 1, coil 400 FIG. 4, coil 600 FIG. 6, coil 800 FIG. 8, coil 1400 FIG. 14). The RF antennas 1250 may be controlled, at least in part, by a set of RF transmission units 1260. An RF transmission unit 1260 may provide a signal to a member of the set of RF antennas 1250.

The gradient coils supply 1240 and the RF transmission units 1260 may be controlled, at least in part, by a control computer 1270. The magnetic resonance signals received from the RF antennas 1250 can be employed to generate an image, and thus may be subject to a transformation process like a two dimensional FFT that generates pixilated image data. The transformation can be performed by an image computer 1280 or other similar processing device. The image data may then be shown on a display 1299. While FIG. 12 illustrates an example MRI apparatus 1200 that includes various components connected in various ways, it is to be appreciated that other MRI apparatus may include other components connected in other ways. In one example, MRI apparatus 1200 may include control computer 1270. In one example, a member of the set of RF antennas 1250 may be individually controllable by the control computer 1270.

Returning now to FIG. 1, elements of an apparatus are illustrated. The apparatus includes a base 110 that includes a mechanical attachment 154 for mechanically coupling to a member 100 of two or more different MRI coils. The mechanical attachment 154 may include, for example, a latch or latches. While a latch is illustrated, other mechanical attachments may be employed.

The base 110 also includes an electrical attachment 152 for electrically coupling to the coil 100. The electrical attachment 152 may take different forms. For example, the electrical attachment 152 may include a direct current (DC) connector(s). In one embodiment, when the MRI coil 100 is just a partial coil, the DC connector(s), the elements, and the partial coil may form a complete coil when coil 100 is connected together with base 110. The electrical attachment 152 may take other forms including, for example, a conductive connector(s), a capacitive coupling connector(s), or an inductive coupling connector(s). In one embodiment, when the MRI coil 100 is just a partial coil, the conductive connector(s), the capacitive coupling connector(s), or the inductive coupling connector(s) combined with the elements and the partial coil may form a complete coil when coil 100 is connected together with base 110.

The electrical attachment 152 may pass an RF signal between the base 110 and the MRI coil 100. In one embodiment, the RF signal may be an unamplified RF signal.

The base 110 includes elements for controlling the MRI coil 100 to transmit RF energy that is configured to produce NMR in an object exposed to the RF energy. The RF energy is applied according to a pulse sequence controlled by an MRI apparatus (e.g., apparatus 1200, FIG. 12) that produces a magnetic resonance image from signals received by the MRI coil 100. The elements may include one or more MRI coil channels as illustrated in, for example, FIGS. 3, 5, 7, and 11. The elements may also include a pre-amplifier, a feed circuit, or a decoupling circuit. The base 110 includes a cable 120 for electrically connecting the base 110 to the MRI apparatus.

The apparatus also includes the MRI coil 100. Coil 100 is configured to be mechanically and electrically coupled to the base 110 as illustrated in, for example, FIG. 2. The coil 100 may be a member of a set of different MRI coils that can be attached to and detached from base 110. In one embodiment, the MRI coil 100 includes a copper trace configured to receive RF energy. In one embodiment, the MRI coil 100 includes a complete coil while in another embodiment the MRI coil 100 only includes a partial coil. When the coil 100 only includes a partial coil, then elements that are needed to make a complete coil may be found in base 110.

In one embodiment, the MRI coil 100 includes a unique coil identification circuit that provides information that controls an MRI apparatus to execute computer executable instructions specific to the MRI coil 100 when the MRI coil 100 is coupled to the base 110 and the base 110 is electrically connected to the MR apparatus. For example, a pulse sequence and imaging parameters suitable for imaging a human knee may automatically be loaded into the MRI apparatus when coil 100 is attached to base 110 and base 110 is attached to the MRI apparatus. However, a pulse sequence and imaging parameters suitable for imaging a human foot may automatically be loaded into the MRI apparatus when coil 400 (FIG. 4) is attached to base 110 and base 110 is attached to the MRI apparatus. Different coils will have different unique coil identifiers.

In one embodiment, the unique coil identification provides information generated by the coil 100 to a base or to an MRI apparatus. In another embodiment, the unique coil identification may store information previously provided to the coil by a base or an MRI apparatus and then provide that information generated off the coil 100 to another base or MRI apparatus. For example, the unique identification may store tuning data, performance data, a count of a number of procedures performed using coil 100, or other information. The information provided by coil 100 may be recognized by an MR system when the coil 100 is connected to the MR system through base 110, cable 120 and connector 140.

The unique coil identification provides information that can be used to configure the MR apparatus. The information may control, for example, scan parameters including sequence selection, sequence parameters, field of view (FOV), slice thickness, or anatomy selection. Automating these or other setup parameters facilitates reducing setup time and complexity, which in turn improves workflow and reduces costs.

Once the scan parameters are loaded, the MR system may start to scan sooner than is possible with conventional systems. For example, a scan may start as soon as patient alignment with system and coil is achieved.

In FIG. 1, the MRI coil 100 is configured for imaging a knee. More generally, a detachable and attachable coil may be configured for musculoskeletal imaging. Different coils may be configured to attach to base 110 to facilitate imaging different body parts. For example, an MRI coil may be configured for imaging a human foot, a human ankle, a human knee, a human hand, a human wrist, or a human shoulder. Conventionally, there may have been a coil for the right foot and a coil for the left foot. Example apparatus are not so limited. In one embodiment, base 110 includes a slide assembly 150 that facilitates repositioning the MRI coil 100 in one axis when the MRI coil 100 is coupled to the base 110. For example, the coil 100 may be slid left or right in the base 110 when attached to assembly 150. Thus, using just a single coil, the apparatus may be configured for imaging a right human ankle while the slide assembly 150 is positioned in a first location and for imaging a left human ankle while the slide assembly 150 is positioned in a second, different location. In another embodiment, using just a different single coil, the apparatus may be configured for imaging a right human knee while the slide assembly 150 is positioned in a first location and for imaging a left human knee while the slide assembly 150 is positioned in a second, different location. In another embodiment, using just another single coil, the apparatus is configured for imaging a right human wrist while the slide assembly 150 is positioned in a first location and a left human wrist while the slide assembly 150 is positioned in a second, different location.

In one embodiment, the base 110 includes a pivot assembly that facilitates rotating the MRI coil 100 when the MRI coil is coupled to the base apparatus 110. This may facilitate accommodating various anatomical features that are slightly different from normal or for accommodating particularly large or small anatomical features. Additionally, this may facilitate quickly reconfiguring an assembly of a coil and a base. For example, the assembly may be configured for imaging a right human shoulder while the slide assembly is positioned in a first slide location and the pivot assembly is positioned in a first pivot position, and for imaging a left human shoulder while the slide assembly is positioned in a second slide location and the pivot assembly is positioned in a second pivot position.

Figure 13:
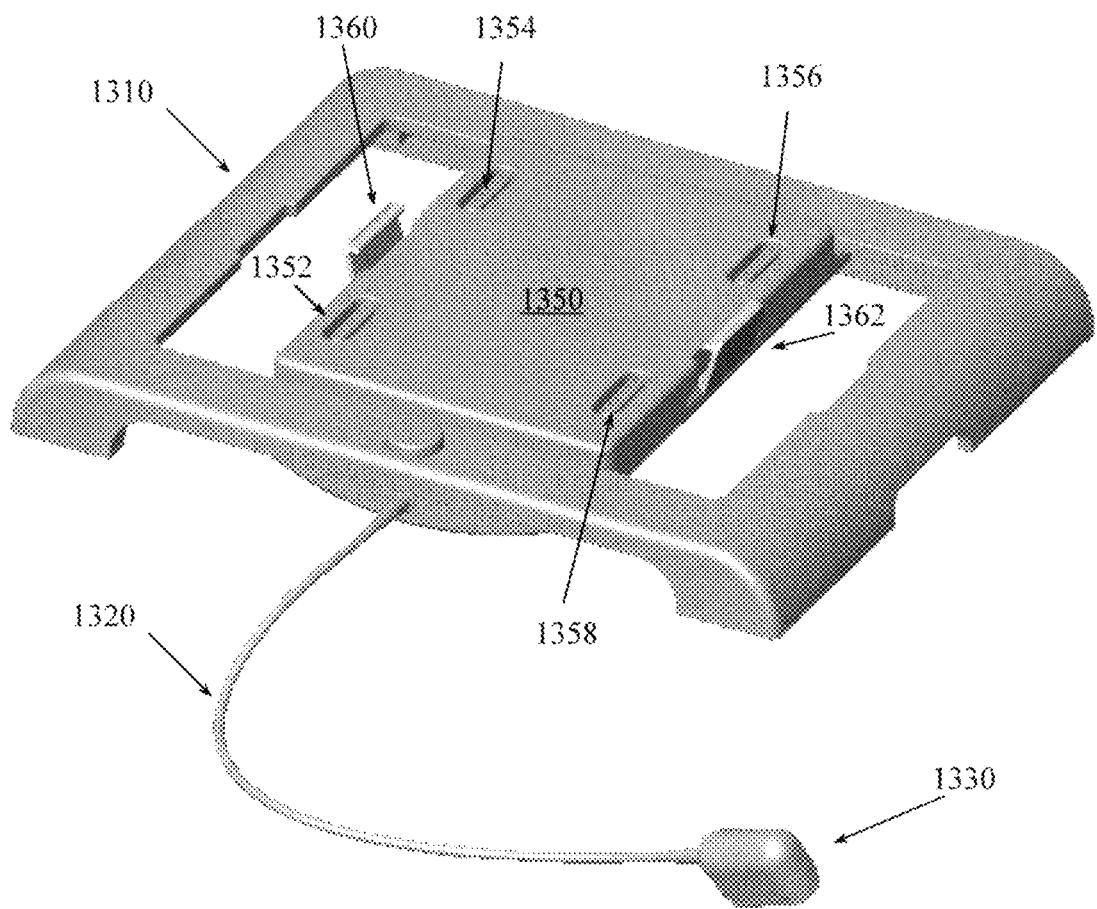
FIG. 13 illustrates an example base configured for use with interchangeable attachable and detachable coils.

FIG. 13 illustrates an example MRI coil base apparatus 1310. Apparatus 1310 includes a mechanical attachment 1360 for mechanically coupling to different MRI coil attachments. The mechanical attachment 1360 includes a latch that makes the different MRI coil attachments attachable to and detachable from the MRI coil base apparatus 1310. While a latch is illustrated, other mechanical connectors may be employed. While two latches 1360 and 1362 are illustrated, a greater or lesser number may be employed.

Apparatus 1310 also includes an electrical attachment 1352 for electrically coupling to different MRI coil attachments. The electrical attachment 1352 includes a connector that passes an RF signal between the MRI coil base apparatus 1310 and the MRI coil. While four electrical attachments 1352, 1354, 1356, and 1358 are illustrated, a greater or lesser number of electrical attachments may be employed. The electrical connector 1352 facilitates having the base 1310 electrically coupled to and in data communication with the MR coil through a direct connection, a capacitive coupling, an inductive coupling, an optical coupling, or an electro/mechanical switch.

Apparatus 1310 also includes a cable 1320 for electrically connecting the MRI coil base apparatus 1310 to an MRI apparatus that produces a magnetic resonance image from signals received by a coil attached to the MRI coil base apparatus 1310. Cable 1320 may terminate at connector 1330.

Apparatus 1310 also includes one or more elements for controlling an attached MRI coil to transmit RF energy configured to produce NMR in an object exposed to the RF energy when the MRI coil is attached to the MRI coil base apparatus 1310. The one or more elements may include, for example, two or more MRI coil channels, a pre-amplifier, a feed circuit, and a decoupling circuit.

Apparatus 1310 includes a slide assembly 1350 that facilitates repositioning an attached MRI coil in one axis when coupled to the MRI coil base apparatus 1310. Apparatus 1310 may also include a pivot assembly that facilitates rotating an MRI coil that is coupled to the MRI coil base apparatus 1310.

Figure 14:
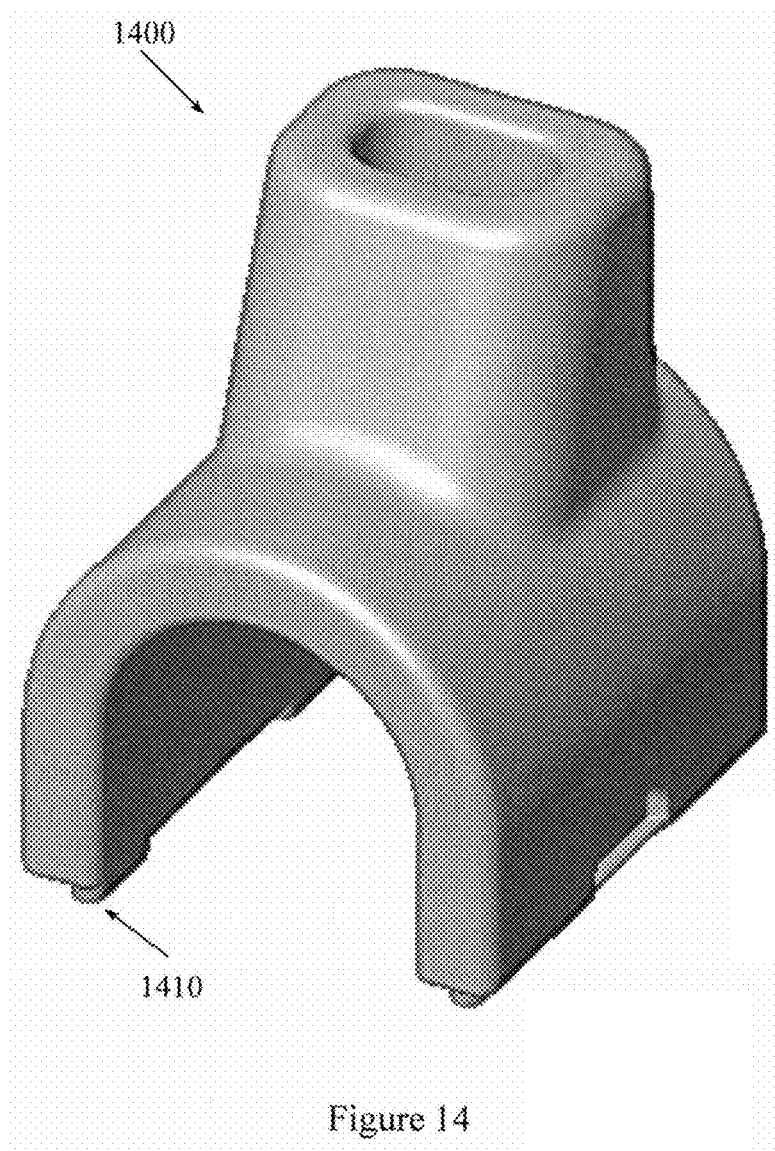
FIG. 14 illustrates an example coil that may be used with an example base configured for use with interchangeable attachable and detachable coils.

FIG. 14 illustrates an example MRI coil 1400. In one embodiment, coil 1400 may be used to image a foot or a knee. When used to image both feet and knees, a lower geometry dimension may be increased to accommodate the knee. More generally, coil 1400 is configured to be mechanically and electrically coupled to an MRI coil base apparatus. Coil 1400 may include a copper trace configured to receive RF energy. In different embodiments, the copper trace may be arranged as a complete coil or as a partial coil. Coil 1400 may also include a unique coil identification circuit that provides information that controls, at least in part, an MRI apparatus. The unique coil identification circuit may cause an MRI apparatus to execute computer executable instructions specific to the MRI coil attachment 1400 when the MRI coil attachment 1400 is coupled to an MRI coil base apparatus and the MRI coil base apparatus is electrically coupled to and in data communication with the MR apparatus. This automatic execution facilitates increasing the efficiency of an MR system.

Apparatus 1400 also includes an electrical attachment 1410 for electrically coupling to an MRI base. The electrical attachment 1410 includes a connector that passes an RF signal between an MRI coil base apparatus and the MRI coil 1400. While a single electrical attachment 1410 is illustrated, a greater number of electrical attachments may be employed. The electrical connector 1410 facilitates having a base electrically coupled to and in data communication with the MR coil 1400 through a direct connection, a capacitive coupling, an inductive coupling, an optical coupling, or an electro/mechanical switch.

The following includes definitions of selected terms employed herein. The definitions include various examples or forms of components that fall within the scope of a term and that may be used for implementation. The examples are not intended to be limiting. Both singular and plural forms of terms may be within the definitions.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

To the extent that the term "includes" or "including" is employed in the detailed description or the claims, it is intended to be inclusive in a manner similar to the term "comprising" as that term is interpreted when employed as a transitional word in a claim.

To the extent that the term "or" is employed in the detailed description or claims (e.g., A or B) it is intended to mean "A or B or both". The term "and/or" is used in the same manner, meaning "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

Although the subject matter has been described in language specific to structural features or methodological acts, it is to be understood that the subject matter defined in the appended claims is not necessarily limited to the specific features or acts described above. Rather, the specific features and acts described above are disclosed as example forms of implementing the claims.

What is claimed is:

1. An apparatus, comprising:
   a base comprising:
      a mechanical attachment for mechanically coupling to a member of two or more different magnetic resonance imaging (MRI) coils, wherein the two or more different MRI coils comprise a first MRI coil configured for imaging a first anatomical region and a different second MRI coil configured for imaging a second anatomical region different than the first anatomical region, wherein each of the first anatomical region and the second anatomical region is one of: a human foot, a human ankle, a human knee, a human hand, a human wrist, or a human shoulder; and
      an electrical attachment for electrically coupling to the member of the two or more different MRI coils; and
   an MRI coil configured to be mechanically and electrically coupled to the base, the MRI coil being a member of the two or more different MRI coils.

2. The apparatus of claim 1, where the base comprises one or more elements for controlling the MRI coil to transmit radio frequency (RF) energy configured to produce nuclear magnetic resonance (NMR) in an object exposed to the RF energy, where the RF energy is applied according to a pulse sequence controlled by an MRI apparatus that produces a magnetic resonance image from signals received by the MRI coil.

3. The apparatus of claim 2, where the one or more elements include two or more MRI coil channels.

4. The apparatus of claim 3, where the one or more elements include a pre-amplifier, a feed circuit, and a decoupling circuit.

5. The apparatus of claim 4, where the base comprises a cable for electrically connecting the base to the MRI apparatus.

6. The apparatus of claim 2, where the MRI coil comprises a copper trace configured to receive RF energy.

7. The apparatus of claim 6, where the MRI coil comprises a complete coil.

8. The apparatus of claim 6, where the MRI coil comprises a partial coil.

9. The apparatus of claim 5, where the MRI coil includes a unique coil identification circuit that provides information that controls the MRI apparatus to execute computer executable instructions specific to the MRI coil when the MRI coil is coupled to the base and the base is electrically connected to the MR apparatus.

10. The apparatus of claim 9, where the unique coil identification circuit stores information provided to the MRI coil by the base or the MRI apparatus.

11. The apparatus of claim 2, where the MRI coil is one of the first MRI coil or the second MRI coil.

12. The apparatus of claim 5, where the base includes a slide assembly that facilitates repositioning the MRI coil in one axis when the MRI coil is coupled to the base.

13. The apparatus of claim 12, where the MRI coil is configured for imaging a right human ankle while the slide assembly is positioned in a first location and for imaging a left human ankle while the slide assembly is positioned in a second, different location.

14. The apparatus of claim 12, where the MRI coil is configured for imaging a right human knee while the slide assembly is positioned in a first location and for imaging a left human knee while the slide assembly is positioned in a second, different location.

15. The apparatus of claim 12, where the MRI coil is configured for imaging a right human wrist while the slide assembly is positioned in a first location and a left human wrist while the slide assembly is positioned in a second, different location.

16. The apparatus of claim 12, where the base includes a pivot assembly that facilitates rotating the MRI coil when the MRI coil is coupled to the base apparatus.

17. The apparatus of claim 16, where the MRI coil is configured for imaging a right human shoulder while the slide assembly is positioned in a first slide location and the pivot assembly is positioned in a first pivot position, and for imaging a left human shoulder while the slide assembly is positioned in a second slide location and the pivot assembly is positioned in a second pivot position.

18. The apparatus of claim 17, where the MRI coil has a symmetric design.

19. The apparatus of claim 1, where the mechanical attachment comprises one or more latches.

20. The apparatus of claim 1, where the electrical attachment comprises one or more direct current (DC) connectors.

21. The apparatus of claim 20,
   where the base comprises one or more elements for controlling the MRI coil to transmit radio frequency (RF) energy configured to produce nuclear magnetic resonance (NMR) in an object exposed to the RF energy, where the RF energy is applied according to a pulse sequence controlled by an MRI apparatus that produces a magnetic resonance image from signals received by the MRI coil, and
   where the MRI coil comprises a partial coil and where the one or more DC connectors, the one or more elements, and the partial coil form a complete coil.

22. The apparatus of claim 1, where the electrical attachment comprises a conductive connector, a capacitive coupling connector, or an inductive coupling connector.

23. The apparatus of claim 22,
   where the base comprises one or more elements for controlling the MRI coil to transmit radio frequency (RF) energy configured to produce nuclear magnetic resonance (NMR) in an object exposed to the RF energy, where the RF energy is applied according to a pulse sequence controlled by an MRI apparatus that produces a magnetic resonance image from signals received by the MRI coil, and
   where the MRI coil comprises a partial coil and where the one or more elements, the partial coil, and the conductive connector, the capacitive coupling connector, or the inductive coupling connector form a complete coil.

24. The apparatus of claim 20, where the one or more DC connectors pass an RF signal between the base and the MRI coil.

25. The apparatus of claim 24, where the RF signal is an unamplified RF signal.

26. The apparatus of claim 22, where the conductive connector, the capacitive coupling connector, or the inductive coupling connector pass an RF signal between the base and the MRI coil.

27. The apparatus of claim 26, where the RF signal is an unamplified RF signal.

28. A magnetic resonance imaging (MRI) coil base apparatus, comprising:
- a mechanical attachment for mechanically coupling to a member of two or more different MRI coil attachments, where the member is attachable to and detachable from the MRI coil base apparatus;
- an electrical attachment for electrically coupling to the member, where the electrical attachment comprises one or more connectors that pass a radio frequency (RF) signal between the MRI coil base apparatus and the member;
- a cable for electrically connecting the MRI coil base apparatus to an MRI apparatus that produces a magnetic resonance image from signals received by the member when the member is attached to the MRI coil base apparatus; and
- one or more elements for controlling the member to transmit RF energy configured to produce nuclear magnetic resonance (NMR) in an object exposed to the RF energy when the member is attached to the MRI coil base apparatus, where the one or more elements include two or more MRI coil channels, a pre-amplifier, a feed circuit, and a decoupling circuit.

29. The MRI coil base apparatus of claim 28, comprising:
- a slide assembly that facilitates repositioning the member in one axis when the member is coupled to the MRI coil base apparatus, and
- a pivot assembly that facilitates rotating the member when the member is coupled to the MRI coil base apparatus.

30. The MRI coil base apparatus of claim 28, where the electrical attachment provides a direct connection, a capacitive coupling, an inductive coupling, an optical coupling, or an electro/mechanical switch between the MRI coil base apparatus and the member.

31. A magnetic resonance imaging (MRI) coil attachment configured to be mechanically and electrically coupled to an MRI coil base apparatus, comprising:
- a copper trace configured to receive radio frequency (RF) energy, the copper trace being arranged as a complete coil or as a partial coil;
- a unique coil identification circuit that provides information that controls an MRI apparatus to execute computer executable instructions specific to the MRI coil attachment when the MRI coil attachment is electrically coupled to and in data communication with the MRI coil base apparatus and the MRI coil base apparatus is electrically coupled to and in data communication with the MR apparatus,
- where the MRI coil attachment is configured for musculoskeletal imaging.

32. The MRI coil attachment of claim 31, where the MRI coil base apparatus electrically couples to the MR coil attachment through a direct connection, a capacitive coupling, an inductive coupling, an optical coupling, or an electro/mechanical switch.

* * * * *